United States Patent
Hörle et al.

(10) Patent No.: US 10,575,995 B2
(45) Date of Patent: Mar. 3, 2020

(54) INTIMATE SKIN CONDITIONER VEIL

(71) Applicant: Essity Hygiene and Health Aktiebolag, Göteborg (SE)

(72) Inventors: Magdalena Hörle, Göteborg (SE); Karin Alenius, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/313,752

(22) PCT Filed: Jun. 28, 2016

(86) PCT No.: PCT/SE2016/050651
§ 371 (c)(1),
(2) Date: Dec. 27, 2018

(87) PCT Pub. No.: WO2018/004404
PCT Pub. Date: Jan. 4, 2018

(65) Prior Publication Data
US 2019/0350770 A1    Nov. 21, 2019

(51) Int. Cl.
*A61F 13/472* (2006.01)
*A61F 13/84* (2006.01)
*A61F 13/511* (2006.01)

(52) U.S. Cl.
CPC ........ *A61F 13/47236* (2013.01); *A61F 13/84* (2013.01); *A45D 2200/1036* (2013.01); *A61F 13/511* (2013.01)

(58) Field of Classification Search
CPC .............. A61F 13/472; A61F 13/47236; A61F 13/47245; A61F 13/475; A61F 13/4752;
(Continued)

(56) References Cited

U.S. PATENT DOCUMENTS 3,310,053 A * 3/1967 Greenwood ............. A41C 1/00
                                                              450/153
4,155,360 A    5/1979 Erickson
(Continued)

FOREIGN PATENT DOCUMENTS

DE    202012010640 U1    2/2013
EP         0521016 A1    1/1993
(Continued)

OTHER PUBLICATIONS

International Search Report (PCT/ISA/210) dated Mar. 20, 2017, by the Swedish Patent Office as the International Searching Authority for International Application No. PCT/SE2016/050651.
(Continued)

*Primary Examiner* — Kari K Rodriguez
(74) *Attorney, Agent, or Firm* — Buchanan Ingersoll & Rooney P.C.

(57) ABSTRACT

An intimate skin conditioner veil, configured to be positioned in an undergarment so that it covers the mons pubis in front of the anterior labia commissure of a female user, without covering any part of the vulval vestibule area of the user, wherein the veil has a longitudinal central line extending in the longitudinal direction thereof, and a first extension in the longitudinal direction, between a front end and a rear end of the veil, and a second extension in a transverse direction perpendicular to the longitudinal central line, and wherein the veil includes a front edge and first and second side edges, and a main portion having a length in the longitudinal direction of the veil, the veil has a total longitudinal length. The length of the main portion is at least 50% of the total longitudinal length of the veil.

20 Claims, 5 Drawing Sheets

(58) Field of Classification Search
CPC ...... A61F 13/4755; A61F 5/443; A61F 5/455; A61F 13/514; A61F 13/52; A61F 2013/5144
USPC .......................................................... 128/891
See application file for complete search history.

(56) References Cited

U.S. PATENT DOCUMENTS

| | | | |
|---|---|---|---|
| 4,553,550 A | 11/1985 | Hattori | |
| D457,689 S * | 5/2002 | Griffiths | D29/100 |
| 7,934,507 B2 * | 5/2011 | Brooks | A41B 9/04 128/873 |
| 8,637,728 B2 * | 1/2014 | Fingal | D04H 5/03 604/367 |
| 2003/0206979 A1 | 11/2003 | Dvoracek et al. | |
| 2006/0121811 A1 | 6/2006 | Mangold et al. | |
| 2006/0206077 A1 | 9/2006 | Warren et al. | |
| 2008/0249491 A1 | 10/2008 | Young et al. | |
| 2009/0062753 A1 | 3/2009 | Ma | |
| 2009/0155325 A1 | 6/2009 | Magin et al. | |
| 2009/0181073 A1 | 7/2009 | Renzin et al. | |
| 2010/0152687 A1 * | 6/2010 | Carlozzi | A41B 9/04 604/359 |
| 2010/0249741 A1 | 9/2010 | Fingal et al. | |
| 2013/0042394 A1 | 2/2013 | Wexler | |
| 2013/0096525 A1 * | 4/2013 | Hermansson | A61F 13/471 604/369 |
| 2014/0230831 A1 * | 8/2014 | Zaltsberg | A61F 5/30 128/891 |
| 2015/0257943 A1 * | 9/2015 | Noel | A61F 13/472 604/369 |
| 2016/0128921 A1 | 5/2016 | Husmark et al. | |
| 2017/0216080 A1 * | 8/2017 | Moscherosch | A61F 13/15203 |
| 2019/0201252 A1 * | 7/2019 | Koehler | A61F 13/15 |

FOREIGN PATENT DOCUMENTS

| | | |
|---|---|---|
| EP | 1133961 A1 | 9/2001 |
| JP | 2015017349 A | 1/2015 |
| RU | 2415659 C1 | 4/2011 |
| WO | 2006014693 A1 | 2/2006 |
| WO | 2007114742 A1 | 10/2007 |
| WO | 2008147264 A1 | 12/2008 |
| WO | 2009025699 A1 | 2/2009 |

OTHER PUBLICATIONS

International Search Report (PCT/ISA/210) dated Mar. 20, 2017, by the Swedish Patent Office as the International Searching Authority for International Application No. PCT/SE2016/050654.
International Search Report (PCT/ISA/210) dated Mar. 20, 2017, by the Swedish Patent Office as the International Searching Authority for International Application No. PCT/SE2016/050655.
Written Opinion (PCT/ISA/237) dated Mar. 20, 2017, by the Swedish Patent Office as the International Searching Authority for International Application No. PCT/SE2016/050651.
Written Opinion (PCT/ISA/237) dated Mar. 20, 2017, by the Swedish Patent Office as the International Searching Authority for International Application No. PCT/SE2016/050654.
Written Opinion (PCT/ISA/237) dated Mar. 20, 2017, by the Swedish Patent Office as the International Searching Authority for International Application No. PCT/SE2016/050655.
International Preliminary Report on Patentability (PCT/IPEA/409) dated Jun. 16, 2018, by the European Patent Office as the International Searching Authority for International Application No. PCT/SE2016/050651.
Office Action (Examination report No. 1 for standard patent application) dated May 30, 2019, by the Australian Patent Office in corresponding Australian Patent Application No. 2016412537. (2 pages).
Office Action (Examination report No. 2 for standard patent application) dated Jul. 24, 2019, by the Australian Patent Office in corresponding Australian Patent Application No. 2016412537. (3 pages).
Office Action dated Oct. 3, 2019, by the Federal Service for Intellectual Property in Russian Patent Application No. 2019101224/04(001951) and an English Translation of the Office Action. (15 pages).

* cited by examiner

INTIMATE SKIN CONDITIONER VEIL

TECHNICAL FIELD

The present disclosure relates to an intimate skin conditioner veil configured to be positioned in an undergarment so that it covers the V-zone of a female user, i.e. covering the mons pubis in front of the anterior labia commissure of a female user, without covering any part of the vulval vestibule area of the user.

BACKGROUND ART

Shaving or removing hair from the genital area is an essential part of daily beauty care for today's women. However, removing hair from the genital area of a female user may leave the skin in that area swollen, dry and often irritated. Cremes and lotions can be used to relieve skin irritation, but may stain the undergarment of the user. The absence of hair in the genital area after hair removal may also lead to the garments of the user chafing the skin and to undesirable skin problems when the skin becomes moist due to the undergarment lying too closely against the skin.

SUMMARY OF THE DISCLOSURE

The present disclosure aims at providing a product, which can avoid or mitigate the problems that may arise after hair removal in the V-zone, said V-zone being a part of the genital area of a female user comprised of mons pubis in front of the anterior labia commissure in the genital area of a female user. The present disclosure thus relates to an intimate skin conditioner veil, which is configured to be positioned in an undergarment so that it covers the mons pubis in front of the anterior labia commissure of the female user, without covering any part of the vulval vestibule area of the user, wherein the veil has a longitudinal central line extending in the longitudinal direction of the veil, and a first extension in the longitudinal direction, between a front end and a rear end of the veil, and a second extension in a transverse direction perpendicular to the longitudinal central line, and wherein the veil comprises a front edge and first and second side edges. The veil comprises a main portion having a length L1 in the longitudinal direction of the veil. The veil has a total longitudinal length L2. The length L1 of the main portion is at least 50% of the total longitudinal length L2 of the veil, wherein the main portion is bounded by a straight front transversal line between front transition points and the first and second side edges, and tapers towards the rear end of the veil, the main portion preferably being reflection symmetric about the longitudinal central line. The veil has a garment facing side and a skin contacting side, the garment facing side and the skin contacting side facing away from one another. The veil further comprises a garment facing layer arranged on the garment facing side of the veil, and a space creating layer arranged on the skin contacting side of the veil.

The intimate skin conditioner veil may preferably further comprise a rear edge which extends substantially in the transverse direction of the veil, at the rear end of the veil, whereby the first and second side edges extend between the front transition points and rear transition points, and the main portion extends in the longitudinal direction between the front transversal line and a straight rear transversal line between the rear transition points, wherein the straight rear transversal line is perpendicular to the longitudinal central line. The main portion may preferably have a front transversal width W1 and a rear transversal width W2, wherein the ratio W1/W2 is 1.1-6.6, preferably 1.5-4.2, more preferably 2.8-3.5. The ratio of the longitudinal lengths L1/L2 is preferably 0.5-1, more preferably 0.6-0.9, most preferably 0.75-0.85. The longitudinal length L1 of the main portion is preferably 60-170 mm, and the total longitudinal length L2 of the veil is preferably 60-220 mm, more preferably 80-150 mm, most preferably 90-120 mm. The main portion preferably has a front transversal width W1 of 100-240 mm, more preferably 140-210 mm, most preferably 155-175 mm and a rear transversal width W2 of 25-95 mm, more preferably 40-80 mm, most preferably 55-70 mm.

The main portion advantageously is tapered such that a straight line between the front transition point and the rear transition point, is inclined in relation to the rear transversal line at an angle $v^1$, which is greater than 90°, preferably 95-160°, more preferably 100-130°, most preferably 105-125°, and that an angle $v^2$ between said straight line and the front transversal line is $v^2=180°-v^1$.

The first and second side edges may advantageously have a curved concave shape between the front and rear transition points. In addition, the main portion may comprise a front main portion located between the front transversal line and a straight intermediate transversal line, and a rear main portion located between the rear transversal line and the intermediate transversal line, wherein longitudinal length of the front main portion is the same as the longitudinal length of the rear main portion, and wherein the curved concave shape of the first and second side edges changes curvature at an intermediate transition point, but runs in the same direction of curvature, wherein the intermediate transition point is located in the rear main portion between the intermediate transversal line and the rear transversal line. The main portion preferably has an intermediate transversal width of 65-90 mm at the intermediate transversal line. Preferably, the first and second side edges changes curvature such that a straight line between is inclined in relation to the rear transversal line at an angle α, which is >90°, and a straight line between the front transition point and the intermediate transition point is inclined in relation to the front transversal line at angle β, which is <180°−α. The angle α is preferably smaller than the angle $v^1$ between the rear transversal line and the straight line between the rear transition point and the front transition point, and the angle β is preferably smaller than the angle $v^2$ between the straight line and the front transversal line.

The intimate skin conditioner veil should preferably have a Gurley stiffness of 5-300 mgf, more preferably 5-100 mgf. The space creating layer may preferably be a combined layer, comprising a loft layer and a top sheet, the loft layer being positioned between the garment facing layer and the top sheet. The loft layer of the space creating layer may suitably have a basis weight of 15-100 gsm and a thickness of 0.5-3.5 mm. Alternatively, the space creating layer may be a multilayer layer comprising a loft portion and a top sheet portion, the loft portion being positioned between the garment facing layer and the top sheet portion. The top sheet is suitably a nonwoven material comprising natural and/or synthetic fibres, and preferably has a basis weight of 8-100 gsm. The garment facing layer is suitably a breathable back sheet, preferably comprising a breathable plastic film or a nonwoven material, such as combinations of spunbond-meltblown layers. The intimate skin conditioner veil should preferably have a moisture vapour transmission rate greater than 1000 g/m$^2$/24 h, preferably 1300-1600 g/m$^2$/24 h. The thickness of the intimate skin conditioner veil is preferably 0.6-3.8 mm.

Fastening means may suitably be positioned on the garment facing side of the veil, preferably in the form of one or more adhesive or friction areas. The loft layer may be smaller than the garment facing layer and the top sheet. The layers comprised in the veil may suitably be connected by adhesive or ultrasound welded joints.

The intimate skin conditioner veil may further comprising a head portion extending between the front straight line and the front edge, which head portion may comprise at least one protuberance, suitably having a convex shape. The head portion may comprise at least one recess, suitably having a concave shape, and suitably being positioned symmetrically about the longitudinal central line. At least one protuberance may be located on each side of the recess. The intimate skin conditioner veil may also comprise a tail portion extending between the rear transversal line and the rear edge. The tail portion may comprise at least one protuberance and/or recess.

The intimate skin conditioner veil may advantageously comprise an additive composition in the form of a skin well-being agent or a carrier substance carrying a skin well-being agent. The additive composition is preferably comprised within or on the space creating layer.

BRIEF DESCRIPTION OF THE DRAWINGS

Other features and advantages disclosed herein will become more apparent from the following detailed description of illustrative embodiments when read in conjunction with the attached drawings, wherein.

DETAILED DESCRIPTION

The present disclosure relates to a product in the form of an intimate skin conditioner veil, which is configured to be positioned in an undergarment so that it covers the mons pubis in front of the anterior labia commissure of a female user, without covering any part of the vulval vestibule area of the user. The part of the female genital area comprised of the mons pubis in front of the anterior labia commissure of a female user, is referred to as the "V-zone".

In an illustrative embodiment, the intimate skin conditioner veil is configured to be positioned in an undergarment so that it contacts the mons pubis in front of the anterior labia commissure of a female user, without contacting any part of the vulval vestibule area of the user.

Accordingly, the intimate skin conditioner veil is essentially different from common hygiene products, which are intended to protect the garments of the wearer, typically by absorbing various body fluids excreted by the wearer. One purpose of the present intimate skin conditioner veil is to protect the skin in the genital area while reducing the risk of absorption of vaginal fluids besides body perspiration. The veil is therefore substantially non-absorbent.

By substantially non-absorbent it is meant that the veil can absorb 0.9% by weight sodium chloride solution in an amount of 0-2 times its own weight. For example, to be substantially non-absorbent the veil can be formed from any single material or combination of materials, which include but are not limited to materials composed of a nonwoven material, e g spunbonded, meltblown, carded, hydroentangled, wetlaid, materials essentially consisting of non-absorbent fibers, i.e. at least 95% of the fibers are non-absorbent fibers, such as at least 99%, or at least 100% of the fibers in the material are non-absorbent fibers. Non-absorbent fibers in the fibrous can be selected from polyolefins, polyesters, polyamides and blends and combinations thereof.

The hair in the genital area acts as a shield against external mechanical stress, and creates an air gap between the skin and the undergarment that contributes to some airiness. When most or all of the hair has been removed, the undergarment material tends to lie more closely against the skin and there is a greater risk that the area becomes moist, which may increase the risk of bacterial growth and odour problem. Skin that has been shaved can also be negatively affected by the shaving itself due to mechanical irritation of the hair follicles, which may lead to an increased risk of infections in the hair follicles. Skin irritation can also be caused by mechanical stress on the skin when the user is moving, as the garment material lies very close to the skin.

The intimate skin conditioner veil serves to act as a protective barrier between the skin and the undergarment material, and to create a space between the skin and the undergarment material. The veil has a garment facing side and a skin contacting side, the garment facing side and the skin contacting side facing away from one another. The veil comprises a garment facing layer arranged on the garment facing side of the veil, and a space creating layer arranged on the skin contacting side of the veil. The veil is configured to be positioned in the undergarment, and therefore preferably comprises fastening means positioned on the garment facing side, most preferably in the form of one or more adhesive or friction areas. For example, adhesive or friction areas can be formed from any single material or combination of materials, which include but are not limited to hooks, friction adhesives, clips, pressure sensitive fastening adhesive. The veil is preferably not attached to the skin of the wearer, and it is therefore preferably essentially free from any adhesive on the skin contacting side.

Figure 1:
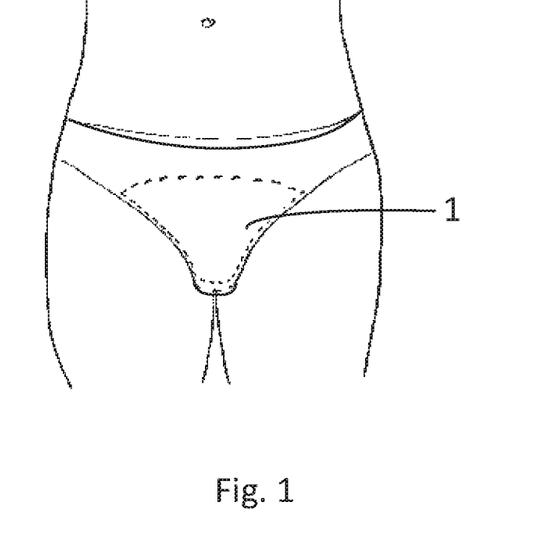
FIG. 1 shows an illustrative embodiment of a veil placed in a panty.
Figure 2:
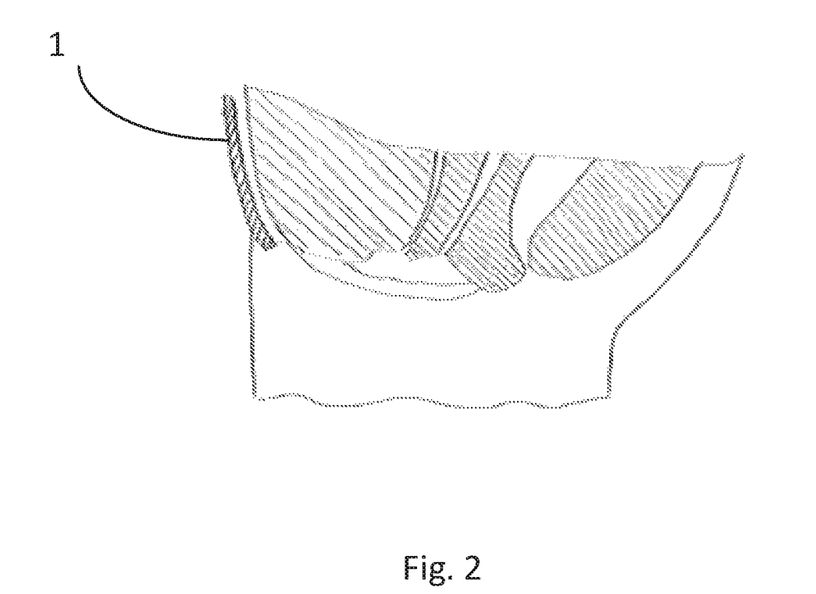
FIG. 2 shows a cross section of the female anatomy of a wearer and an illustrative embodiment of a veil covering the mons pubis in front of the anterior labia commissure of the wearer.

As indicated above, the veil is configured to be worn so that it covers the mons pubis in front of the anterior labia commissure of a female user, without covering any part of the vulval vestibule area of the user. The mons pubis, also known as mons Venus or mons veneris, is a rounded mass of fatty tissue found over the pubic symphysis of the pubic bones. In human females, the mons pubis forms the anterior portion of the vulva. It divides into the labia majora, on either side of the furrow known as the pudendal cleft that surrounds the labia minora, clitoris, urethra, vaginal opening, and other structures of the vulval vestibule. FIGS. 1 and 2 show how the veil is to be worn. FIG. 1 illustrates how the veil 1 is placed in a panty, such that it covers the mons pubis in front of the anterior labia commissure. FIG. 2 shows a cross section of the female anatomy of a wearer and illustrates how the veil 1 covers the mons pubis 22 in front of the anterior labia commissure 23, and how it does not cover any part of the vulval vestibule area 24.

The intimate skin conditioner veil is configured to have a shape that essentially follows the anatomy of the wearer in the genital area. This is accomplished by a main portion of the veil. The main portion preferably has the general shape of a truncated triangle, so that the veil is wider at a front end towards the abdomen of the user, and narrower at a rear end towards the vulval vestibule area. Although a truncated triangular main portion is preferred, the veil may alternatively have a non-truncated triangular shape, with the base of the triangle at the front end and the top of the triangle at the rear end. Further, the intimate skin conditioner veil is preferably very pliable and very thin, as will be described in further detail below.

The intimate skin conditioner veil may comprise an additive composition in the form of a skin well-being agent or a carrier substance carrying a skin well-being agent. The skin well-being agent is a substance which has skin conditioning properties, and contributes to increase the comfort of the wearer. The additive composition thus preferably comprises one or more skin softening agents, or cooling agents, or hydrating agents, or combinations thereof.

A "skin softening agent" refers to a substance which is able to increase the moisture content in the skin when topically applied to the skin of the wearer, for example by depositing fat on the skin surface, such as Vaseline. The additive can also include, but is not limited to, mannitol, ammonium glycyrrhizate, caffeine, zinc gluconate, *aesculus hippocastanum* extract, tocopheryl acetate. A "cooling agent" is a substance which is able to convey a freshness or cooling sensation when topically applied to the skin of the wearer. A "carrier substance" is a substance which is able to act as a carrier vehicle for delivering an effective concentration of a skin well-being agent to a wearer's skin. Suitable carrier substances include, but are not limited to, polyethylene glycol, propylene glycol, water, dimethcone, oil, Vaseline or alcohol, or combinations thereof. The additive composition may also include, but is not limited to, solvents, emulsifying agents, fragrances, and preservatives. The additive composition is preferably comprised within or on the space creating layer. It can be applied to the veil by impregnation of the loft layer and/or the top sheet with the composition, or it can be applied on the skin contacting surface of the top sheet, for example by spraying, slot coating or printing. The additive composition may be applied evenly over the surface area of the veil, or may be applied in a pattern, such as, but not limited to, a pattern of dots or stripes.

Outer Contour

Figure 3:
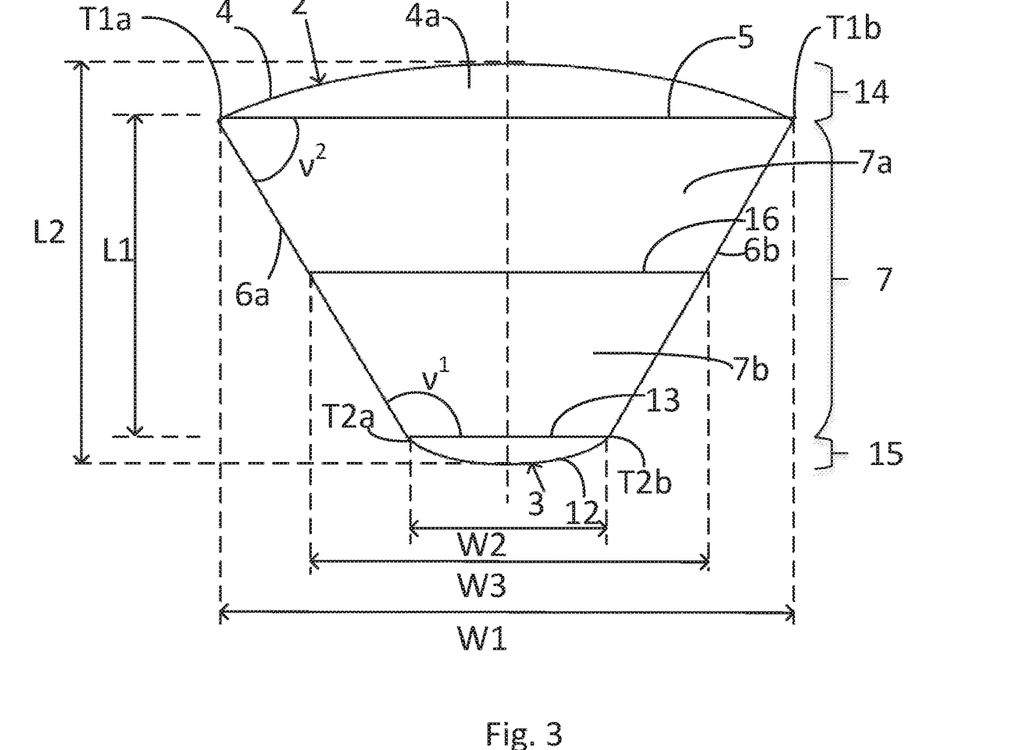
FIG. 3 is a schematic top view of an illustrative embodiment of an intimate skin conditioner veil.

FIG. 3 illustrates an example of an intimate skin conditioner veil of the present disclosure. The veil has a longitudinal central line A extending in the longitudinal direction of the veil; a first extension in the longitudinal direction between a front end 2 and a rear end 3 of the veil; and a second extension in a transverse direction perpendicular to the longitudinal central line A. It comprises a front edge 4 and first and second side edges 6a, 6b, the front edge 4 intersecting the first side edge 6a at a first front transition point T1a and intersecting the second side edge 6b at a second front transition point T1b. The main portion 7 of the veil has a length L1 in the longitudinal direction of the veil, which is at least 50% of the total longitudinal length L2 of the veil 1. The main portion 7 is bounded by a straight front transversal line 5 between the first and second front transition points T1a, T1b, and by the first and second side edges 6a, 6b. The main portion 7 tapers towards the rear end 3 of the veil. The main portion 7 is preferably reflection symmetric about the longitudinal central line A. As indicated above, the main portion 7 is wider at its front end than at its rear end, and it preferably has a front transversal width W1 and a rear transversal width W2 chosen such that the ratio W1/W2 is 1.1-6.6, preferably 1.5-4.2, and more preferably 2.8-3.5.

The intimate skin conditioner veil 1 may further comprise a rear edge 12 which extends substantially in the transverse direction of the veil 1, at the rear end 3 of the veil, the rear edge 12 intersecting the first side edge 6a at a first rear transition point T2a and intersecting the second side edge 6b at a second rear transition point T2b. The first and second side edges 6a, 6b extend between respective ones of the first and second front transition points T1a, T1b and respective ones of the rear transition points T2a, T2b, and the main portion 7 extends in the longitudinal direction between the front transversal line 5 and a straight rear transversal line 13 between the first and second rear transition points T2a, T2b, and the straight rear transversal line 13 is perpendicular to the longitudinal central line A.

The first and second front transition points T1a, T1b and the first and second rear transition points T2a, T2b are located where the outer contour of the veil dramatically changes direction, between a generally longitudinal direction and a generally transversal direction. The front edge 4 of the veil meets the side edges 6a, 6b at the first and second front transition points T1a, T1b, respectively, and the rear edge 12 meets the side edges 6a, 6b at the first and second rear transition points T2a, T2b, respectively, such that the transition points form corners between the front and rear edges 4, 12 and the side edges 6a, 6b. These corners at the transition points can have a sharp shape or may be rounded. The veil shown in FIG. 3 has sharp corners at the front transition points, and the veil shown in FIG. 5 has rounded corners at the front transition points.

Figure 4:
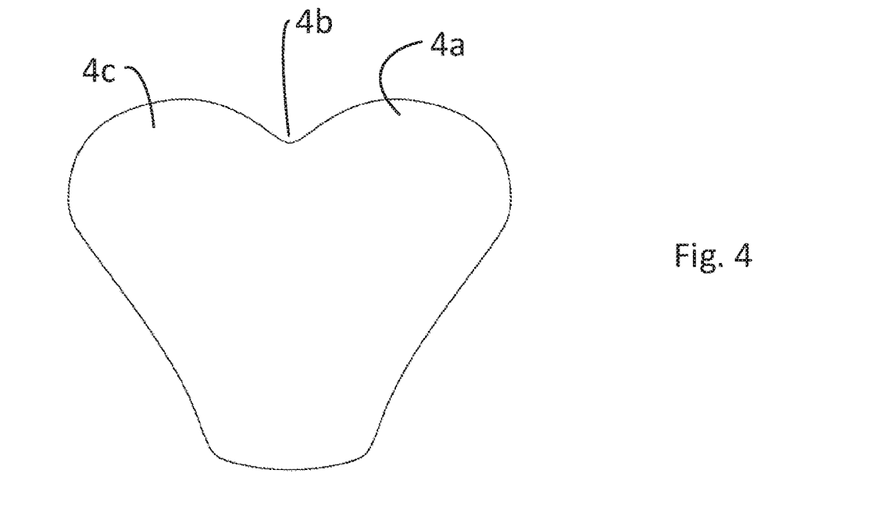
FIG. 4 schematically illustrates the outer contour of another illustrative embodiment of an intimate skin conditioner veil.

The intimate skin conditioner veil 1 may include a head portion 14 at the front end of the veil 1 and/or a tail portion 15. The head portion 14 extends between the front straight line 5 and the front edge 4 of the veil 1. The front edge 4 of the veil 1 is then also the front edge of the head portion 14. The head portion 14 can have various shapes, and can comprise at least one protuberance 4a, which may have a convex shape, as shown in FIG. 3. The head portion 14 may also comprise at least one recess 4b, which may have a concave shape, and which may be positioned symmetrically about the longitudinal central line A, as shown in FIG. 4. The head portion 14 may include at least one protuberance 4a, 4c located on each side of the recess 4b. FIG. 4 illustrates an example of a veil, in which one protuberance 4a, 4c is located on each side of a centrally positioned recess 4b, giving the veil 1 an outer contour resembling a rounded heart. Alternatively, a larger number of protuberances and recesses can be comprised in the head portion 14, for example, but not limited to 1-10 protuberances, and 1-9 recesses. The tail portion 15 extends between the rear transversal line 13 and the rear edge 12. The tail portion 15 portion can have various shapes, and may for example comprise at least one protuberance 12a and/or recess. The head and tail portions 14, 15 serve to further adapt the veil 1 to the anatomy of the wearer, by providing curved front and rear end contours. Fewer protuberances and recesses are preferred for manufacturing reasons, since a veil having a low number of protuberances and recesses in head or veil portion, may lead to a less complicated manufacturing process, while more protuberances and recesses provides a softer edge of the veil, such that the contour of the veil can follow the body shape of the user in an improved manner.

When the veil 1 includes a head portion 14 and/or a tail portion 15, the total longitudinal length L2 of the veil is the combined longitudinal length L1 of the main portion and the longitudinal lengths of the head portion and/or the tail portion. The ratio L1/L2 is preferably 0.5-1, more preferably 0.6-0.9, most preferably 0.75-0.85 so as to follow the anatomy of the wearer. The longitudinal length L1 of the main portion 7 is preferably 60-170 mm, and the total longitudinal length L2 of the veil is 60-220 mm, more preferably 80-150 mm, most preferably 90-120 mm so as to follow the anatomy of the wearer. The main portion preferably has a front transversal width W1 of 100-240 mm, more preferably 140-210 mm, most preferably 155-175 mm and a rear transversal width W2 of 25-95 mm, more preferably 40-80 mm, most preferably 55-70 mm so as to follow the anatomy of the wearer. By choosing the length and width of the veil according to the anatomy of the wearer, it can be ensured that the main portion is sufficiently large to cover the mons pubis in front of the anterior labia commissure.

In order to follow the anatomy of the wearer more closely, the main portion 7 may be tapered such that a straight line 6' between the first front transition point T1a and the first rear transition point T2a is inclined in relation to the front transversal line 5 at an angle $v^2$, which is smaller than 90°, preferably 20-85°, more preferably 50-80°, most preferably 55-75°. The line 6' is inclined in relation to the rear transversal line 13 at an angle $v^1$, which is greater than 90°, preferably 95-160°, more preferably 100-130°, most preferably 105-125°, such that $v^2=180°-v^1$.

In order to further improve the fit of the veil in accordance to the wearer's anatomy, the first and second side edges 6a, 6b of the veil may advantageously have a curved concave shape between the front and rear transition points T1a, T1b, T2a, T2b. The examples of veils shown in FIGS. 4-6 have such curved side edges. A preferred curvature is shown in more detail in FIGS. 5 and 6.

Figure 5:
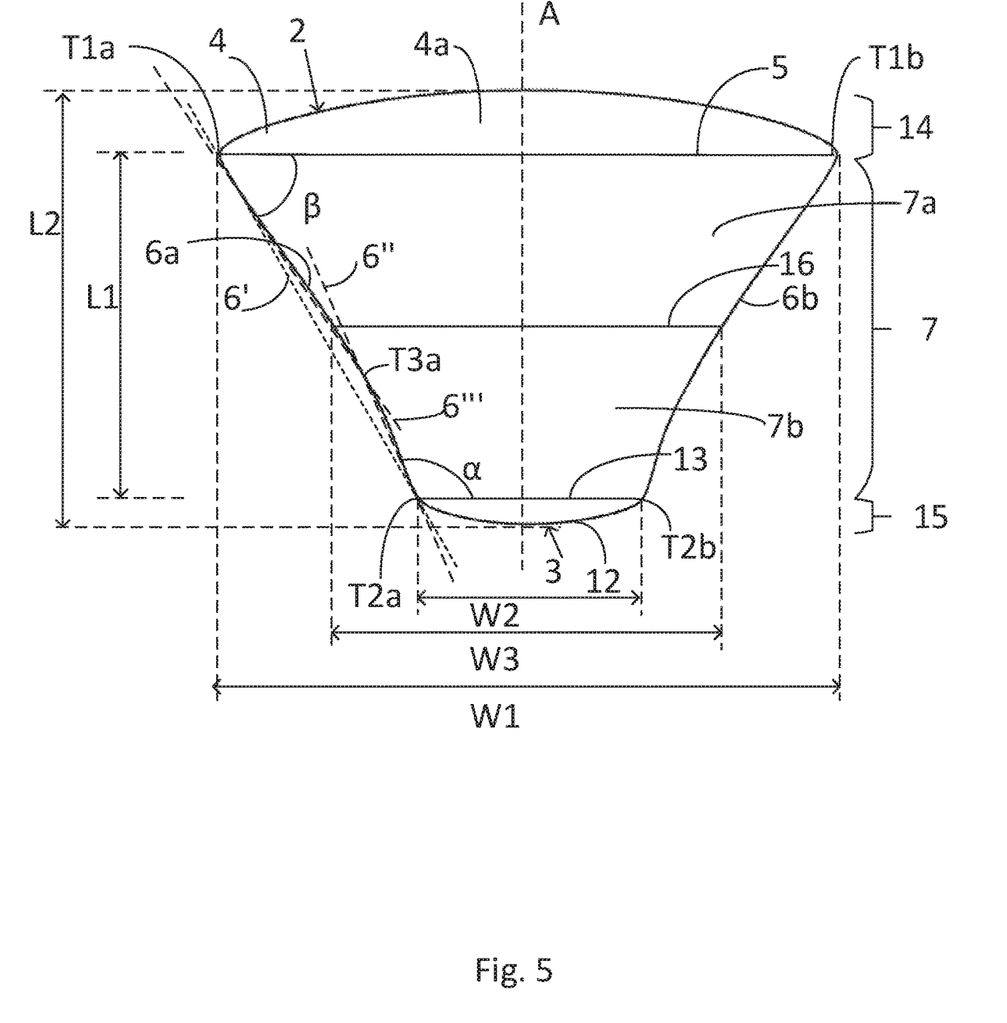
FIG. 5 is a schematic top view of an illustrative embodiment of another intimate skin conditioner veil.

As illustrated in FIG. 5, the main portion 7 of the intimate skin conditioner veil preferably comprises a front main portion 7a located between the front transversal line 5 and a straight intermediate transversal line 16, and a rear main portion 7b located between the rear transversal line 13 and the intermediate transversal line 16. The intermediate transversal line 16 is located at the longitudinal centre of the main portion, such that the longitudinal length of the front main portion 7a is the same as the longitudinal length of the rear main portion 7b. The curved concave shapes of the first and second side edges 6a, 6b preferably change curvature at respective intermediate transition points to adopt respective directions of curvature and continue to run in the same respective directions of curvature. For example, FIG. 5 shows that the curved concave shape of the first side edge 6a changes curvature at an intermediate transition point T3a, and continues to run in the same direction of curvature, and the intermediate transition point T3a is located in the rear main portion 7b between the intermediate transversal line 16 and the rear transversal line 13. The second side edge 6b has a similar shape. The main portion preferably has an intermediate transversal width W3 of 65-90 mm at the intermediate transversal line 16, in order to give a good fit to the wearer's anatomy.

Figure 6:
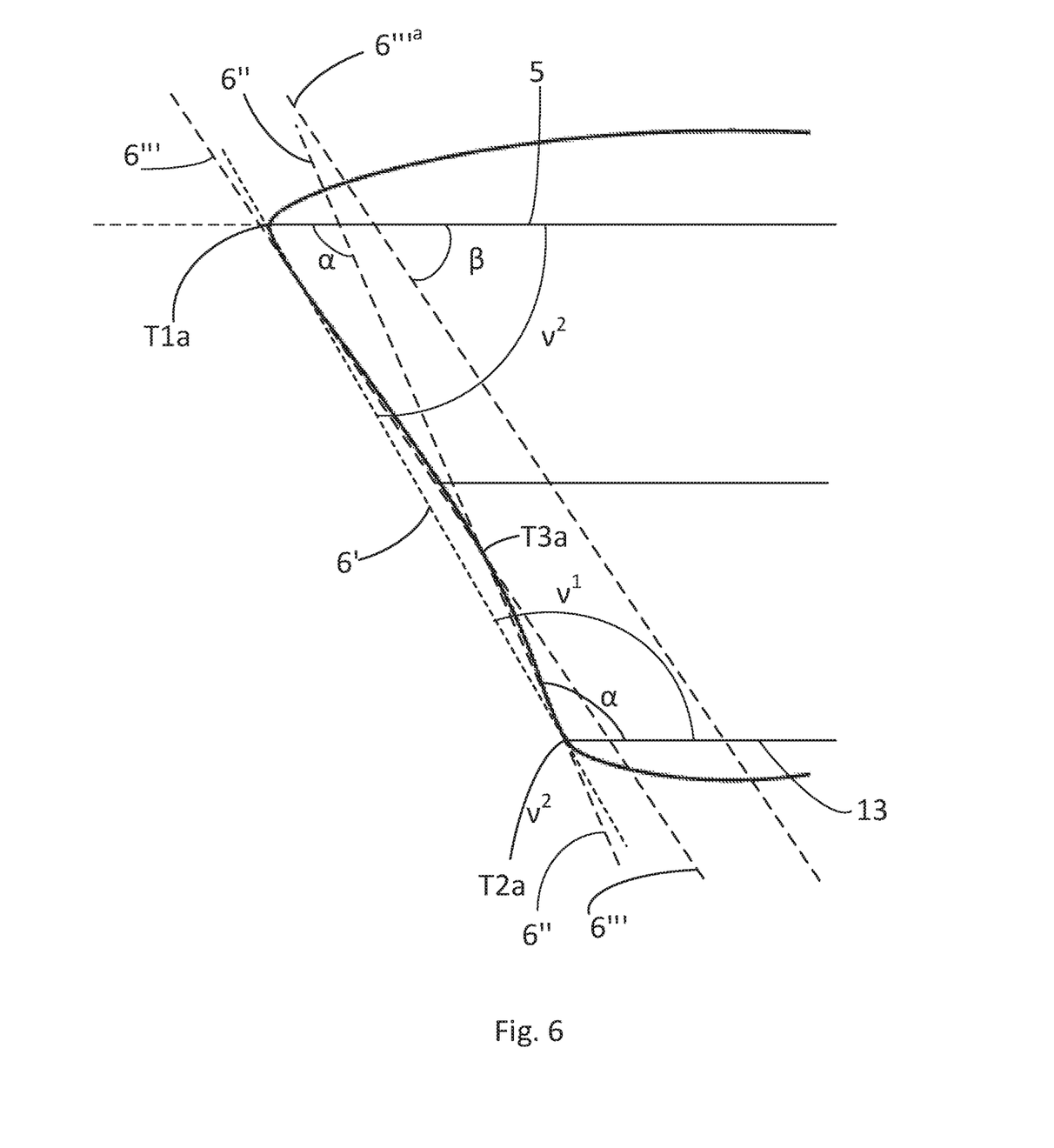
FIG. 6 shows an enlarged portion of the intimate skin conditioner veil shown in FIG. 5.

The fit to the anatomy of the wearer can be further configured to adapt the curvature of the side edges of the veil to the groin anatomy of the wearer. As illustrated in FIGS. 5 and 6, the first and second side edges 6a, 6b may thus advantageously have a curvature, which changes such that a straight line 6''' between the first rear transition point T2a and the intermediate transition point T3a, is inclined in relation to the rear transversal line 13 at an angle α, which is >90°, and a straight line 6''' between the first front transition point T1a and the intermediate transition point T3a is inclined in relation to the front transversal line 5 at angle β, which is <180°−α. Further, the angle α is preferably smaller than the angle $v^1$ between the rear transversal line 13 and the straight line 6' between the first rear transition point T2a and the first front transition point (T1a), and the angle β is preferably smaller than the angle $v^2$ between the straight line 6' and the front transversal line 5. The angle α is preferably 95-160°. A line 6'''$^a$, which is parallel to the line 6''', is drawn in FIG. 6 for illustration purposes.

Materials

In order to conform well to the body of the wearer and to add to the wearing comfort, the intimate skin conditioner veil 1 is preferably very pliable, thin and breathable. The veil comprises a garment facing layer arranged on the garment facing side of the veil, and a space creating layer arranged on the skin contacting side of the veil. The layers comprised in the veil are suitably connected by adhesive or ultrasound welded joints. The intimate skin conditioner veil may include fastening means positioned on the garment facing side, preferably in the form of one or more adhesive or friction areas.

The pliability, stiffness of the intimate skin conditioner veil 1 can be expressed as Gurley Units, and the veil 1 preferably has a Gurley Units of 5-300 mgf, more preferably 5-100 mgf. Gurley Units are measured according to the standard method EDANA/INDA NWSP 090.2.RO (15) modified for measuring the stiffness of an intimate skin conditioner veil product, as described in more detail below. The desired pliability can preferably be obtained by choosing the layers of the veil as described below.

The intimate skin conditioner veil 1 preferably has a total thickness of 0.6-3.8 mm. The space creating layer of the veil may be a combined layer, comprising a loft layer and a top sheet. The loft layer of the space creating layer preferably has a basis weight of 15-100 gsm and a thickness of 0.5-3.5 mm.

The top sheet is preferably a nonwoven material comprising natural and/or synthetic fibres, and preferably has a basis weight of 8-100 gsm, which may be perforated or embossed. Other examples of suitable top sheet materials include, but are not limited to, perforated plastic films, plastic or textile mesh, and fluid permeable layers of foam, such as polyurethane foam based on polyester. Laminates consisting of two or more top sheet material may also be employed, and the top sheet material may be different in different parts of the skin-contacting surface.

The loft layer preferably comprises hydrophobic or hydrophilic nonwoven material, apertured thermoplastic film or open foam material. The nonwoven material may be for example, but is not limited to, air through bonded nonwoven, spunbond, SMS material (spunbond/meltblown/spunbond), carded thermobonded nowoven, or spunlaced (hydroentangled) material.

Alternatively, the space creating layer may be a multilayer layer comprising a loft portion and a top sheet portion, the loft portion being positioned between the garment facing layer and the top sheet portion. The space creating layer may then be a nonwoven material comprising at least two layers integrated into each other, wherein the loft portion preferably comprises spunlaid filaments having a thickness greater than 2.5 dtex, giving an open structure to the loft portion, and the top sheet portion preferably comprises staple fibres, giving a soft feeling. A suitable multilayer layer is described in WO2008147264A1, the disclosure of which is incorporated herein by reference for its description of a multilayer space creating layer. Such a multilayer space creating layer preferably has a basis weight of 15-100 gsm and a thickness of 0.5-3.5 mm.

The loft layer or loft portion of the space creating layer provides an open structure, which contributes to forming a distance between the skin and the garments of the wearer. The loft layer or loft portion can thus function as a replacement for the hair that has been removed, and can thus contribute to airiness and favourable skin conditions in the genital area, particularly in the V-zone. All layers included in the veil can have the same size, or the loft may be smaller than the garment facing layer and the top sheet. With a smaller loft layer, the veil comprises an edge portion along the outer contour, comprising only the garment facing layer and the top sheet, thus making the edges of the veil even thinner and softer.

The garment facing layer is suitably breathable, and preferably comprises a breathable plastic film or a nonwoven material, or a laminate including a breathable plastic film and a layer of nonwoven material. The garment facing layer is preferably also liquid-tight, which means that the material can resist the flow of liquid. Suitable materials for the garment facing layer include, but are not limited to, perforated films, microporous films, macroporous films, nanoporous films, or nowoven or laminates thereof. Examples of nonwoven laminates include, but are not limited to, laminates of spunbond and meltblown, for example SMMS laminate (spunbond/meltblown/spunbond-laminate). The garment facing layer material can include, but is not limited to, renewable material in the form of PLA starch or the like.

The intimate skin conditioner veil 1 preferably does not affect the humidity conditions that prevail in the intermediate space between the skin and the veil more than normal cotton briefs. Each layer of the intimate skin conditioner veil 1 advantageously has a moisture vapour transmission rate greater than 1000 g/m$^2$/24 h, and the intimate skin conditioner veil preferably has a total moisture vapour transmission rate greater than 1000 g/m$^2$/24 h, preferably 1000-6000 g/m$^2$/24 h, more preferably 1300-1600 g/m$^2$/24 h. The garment facing layer thereby allows perspiration generated by the skin to be able to leave the surface of the skin, which reduces moisture on the skin surface and thereby reduces the risk for undesirable skin conditions. The garment facing layer suitably has a basis weight of 18-21 gsm.

Figure 7:
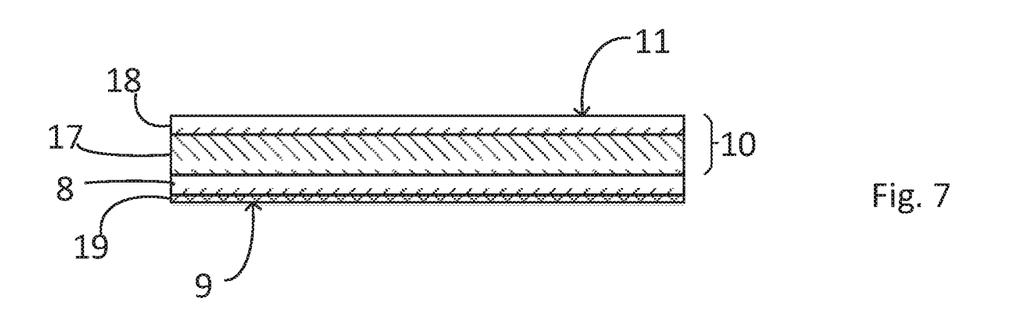
FIG. 7 is a schematic cross sectional view of an illustrative embodiment of an intimate skin conditioner veil.
Figure 8:
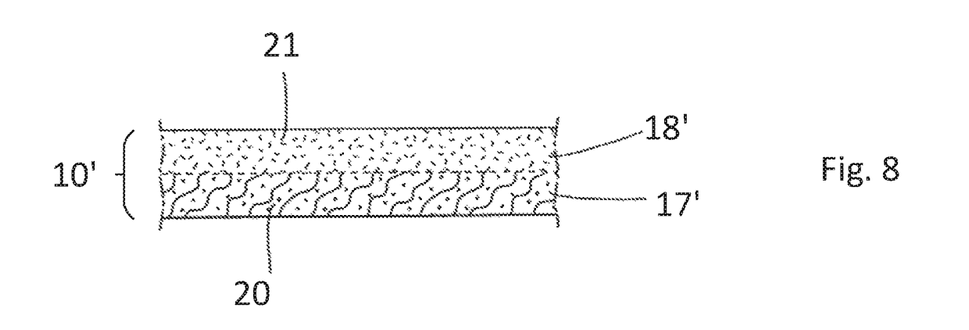
FIG. 8 is a schematic cross sectional view of a multilayer space creating layer used in an illustrative embodiment of an intimate skin conditioner veil.
Figure 9:
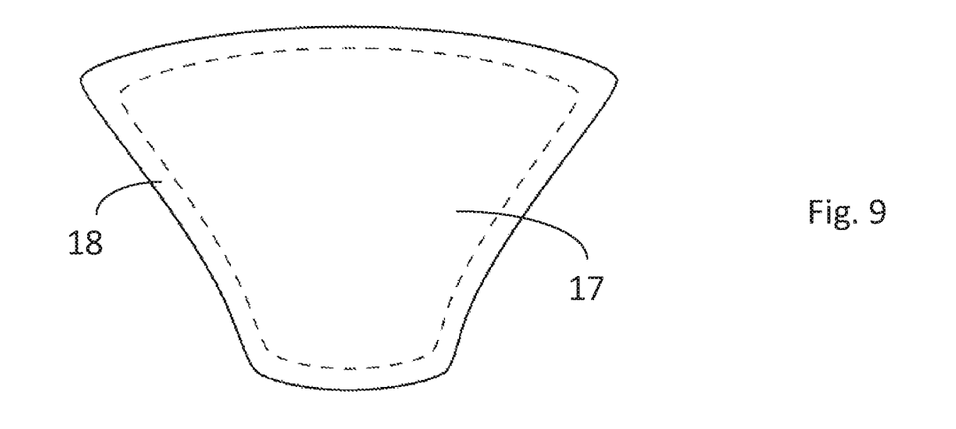
FIG. 9 schematically illustrates an illustrative embodiment of an intimate skin conditioner veil in which the loft layer is smaller than the other layers.

FIG. 7 shows a schematic cross sectional view of the veil. The veil 1 has a garment facing side 9 and a skin contacting side 11, the garment facing side 9 and the skin contacting side 11 facing away from one another. The veil 1 comprises a garment facing layer in the form of a back sheet 8 arranged on the garment facing side 9 of the veil, and a space creating layer 10, arranged on the skin contacting side 11 of the veil. Fastening means 19 are arranged on the garment facing side 9 of the veil. In the example shown in FIG. 7, the space creating layer is a combined layer 10, comprising a loft layer 17 and a top sheet 18, and the loft layer 17 is positioned between the garment facing layer 8 and the top sheet 18. FIG. 8 illustrates an multilayer space creating layer 10' that can be used instead of the combined space creating layer 10 shown in FIG. 7. The multilayer space creating layer 10' comprises a loft portion 17' comprising spunlaid filaments 20 and a top sheet portion 18' comprising staple fibres 21. The multilayer space creating layer 10' is arranged in the veil such that the loft portion 17' is positioned between the garment facing layer 8 and the top sheet portion 18'. FIG. 9 is a schematic top view, showing an example of an intimate skin conditioner veil in which the loft layer 17 is smaller than the top sheet 18 and the back sheet (not shown in FIG. 9).

Measuring Methods

Stiffness

All values for thickness given above for the layers comprised in the intimate skin conditioner veil are obtained by measuring by means of a circular measuring foot having a diameter of 31.5 mm at pressure of 0.2 kPa.

Gurley stiffness is measured according to the standard method EDANA/INDA NWSP 090.2.RO (15). This method is originally intended for measuring stiffness of nonwoven materials, and is therefore modified for measuring stiffness of the entire intimate skin conditioner veil. The method accordingly includes the following additional steps:

remove any release paper from the veil, and cover the attachment adhesive lightly with talcum, or the other equivalent powder;
  cut a representative sample from the center region of the veil, avoiding any folds; and
  if the stiffness of the veil is different along the longitudinal and the transverse axel, let the lowest value represent the article.

Moisture Vapour Transmission Rate

The Moisture Vapour Transmission Rate is a measure of the amount of moisture adsorbed by Calcium-Chloride in a "cup" like container covered with the test specimen from controlled outside air conditions (40±3° C./75±3% relative humidity). The sample holding a cup is a cylinder with an inner diameter of 30 mm and an inside height from bottom to top flange of 49 mm. A flange having a circular opening to match the opening of the cylinder can be fixed by screws, and a silicone rubber sealing ring, matching the inner diameter, fits between the top flange and the cylinder. The test specimen is to be positioned such that it covers the cylinder opening, and can be tightly fixed between the silicone rubber sealing and the upper flange of the cylinder. The test specimen is positioned on the cylinder with the garment facing layer facing the Calcium-Chloride. When testing an intimate skin conditioner veil having adhesive areas applied to the garment facing layer, a plurality (at least 5) test specimens are cut from the veil and tested, and a value representing the MVTR for the entire product is obtained by calculating an average MVTR value of the individual test specimens. The equipment as well as the test specimen should be well adjusted to the temperatures, and the constant temperature/humidity chamber preferably has a size to accommodate up to 30 samples. The absorbent desiccant material is CaCl$_2$, such as can be purchased from Wako Pure Chemical Industries Ltd., Richmond, Va., US under the product designation 030-00525. If kept in a sealed bottle, it can be used directly. It also can be sieved to remove lumps, or excessive amounts of fines, if existing. It also can be dried at 200° C. for about 4 hrs. 15.0±0.02 g of CaCl$_2$ are weighed into the cup, and tapped lightly so as to level it out, such that the surface is about 1 cm from the top of the cup.

The samples, which are cut to about 3.2 cm by 6.25 cm, are placed flat and overlapping with the seal over the opening, and the seal and the top flange are affixed by the screws without over tightening. The total weight of the cup assembly is accurately recorded on a four decimal places scale, and the assembly is placed into the constant temperature/humidity chamber. After 5 hrs (without opening of the chamber), the sample is removed and immediately covered tightly with non-vapour permeable plastic film such as SARAN wrap as commonly used in the U.S. After about 30 mins to allow for temperature equilibration, the plastic film cover is removed and the accurate weight of the assembly is recorded. The MVTR value is then calculated from the moisture increase during these 5 hours through the 3 cm circular opening and then converted to units of $g/m^2/24$ h. For each test, three replicates should be run, the resulting values will be averaged, and the result rounded to the nearest 100 value.

Overall, this method is applicable to thin films, multilayer laminates and the like. Experience has shown that typical standard deviations range between 50 and 250 $g/m^2/24$ h for averaged values of up to about 5000 $g/m^2/24$ h. Due to this range, materials being considered to be essentially vapour impermeable, such as conventional PE films, are reported as having a MVTR of about 200 $g/m^2/24$ h. If the units for an MVTR value are omitted for simplicity, a material "having a MVTR value of 1000" should accurately be a material "having a MVTR value of 1000 $g/m^2/24$ h" according to this method.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An intimate skin conditioner veil, configured to be positioned in an undergarment so that it covers a mons pubis in front of an anterior labia commissure of a female user, without covering any part of a vulval vestibule area of the user, wherein
the veil is substantially non-absorbent, and
the veil has a longitudinal central line extending in the longitudinal direction of the veil, and a first extension in the longitudinal direction, between a front end and a rear end of the veil, and a second extension in a transverse direction perpendicular to the longitudinal central line, and
wherein the veil comprises a front edge and first and second side edges, the front edge intersects the first side edge at a first front transition point and intersects the second side edge at a second front transition point, the veil further comprises a main portion having a length (L1) in the longitudinal direction of the veil, the veil has a total longitudinal length (L2), the length (L1) of the main portion being at least 50% of the total longitudinal length (L2) of the veil, wherein the main portion is bounded by a straight front transversal line between the first and second front transition points and by the first and second side edges, and tapers towards the rear end of the veil, and wherein
the veil has a garment facing side and a skin contacting side, the garment facing side and the skin contacting side face away from one another, and the veil comprises a garment facing layer arranged on the garment facing side of the veil, and a space creating layer arranged on the skin contacting side of the veil.

2. The intimate skin conditioner veil of claim 1, further comprising a rear edge which extends substantially in the transverse direction of the veil, at the rear end of the veil, the rear edge intersecting the first side edge at a first rear transition point and intersecting the second side edge at a second rear transition point, whereby the first and second side edges extend between respective ones of the front transition points and respective ones of the rear transition points, and the main portion extends in the longitudinal direction between the front transversal line and a straight rear transversal line between the first and second rear transition points, wherein the straight rear transversal line is perpendicular to the longitudinal central line.

3. The intimate skin conditioner veil of claim 2, wherein the main portion is tapered such that a straight line between the first front transition point and the first rear transition point, is inclined in relation to the front transversal line at an angle ($v^2$), which is smaller than 90°.

4. The intimate skin conditioner veil of claim 3, wherein an angle ($v^1$) between the straight line and the rear transversal line is ($v^1$)=180°−($v^2$).

5. The intimate skin conditioner veil of claim 2, wherein the first side edge has a curved concave shape between the first front transition point and the first rear transition points, and the second side edge has a curved concave shape between the second front transition point and the second rear transition points.

6. The intimate skin conditioner veil of claim 5, wherein the main portion comprises a front main portion located between the front transversal line and a straight intermediate transversal line, and a rear main portion located between the rear transversal line and the intermediate transversal line, and wherein a longitudinal length of the front main portion is the same as a longitudinal length of the rear main portion, and wherein the curved concave shapes of the first and second side edges each change curvature at respective intermediate transition points to adopt respective directions of curvature, and continue to run in the same respective directions of curvature, wherein the respective intermediate transition points are located in the rear main portion between the intermediate transversal line and the rear transversal line.

7. The intimate skin conditioner veil of claim 6, wherein the main portion has an intermediate transversal width of 65-90 mm at the intermediate transversal line.

8. The intimate skin conditioner veil of claim 6, wherein the first and second side edges change curvature such that a straight line between the first rear transition point and the intermediate transition point, is inclined in relation to the rear transversal line at an angle (α), which is >90°, and a straight line between the first front transition point and the intermediate transition point is inclined in relation to the front transversal line at angle (β), which is <180°−(α).

9. The intimate skin conditioner veil of claim 8, wherein
the angle (α) is smaller than the angle ($v^1$) between the rear transversal line and the straight line between the first rear transition point and the first front transition point, and
the angle (β) is smaller than the angle ($v^2$) between the straight line and the front transversal line.

10. The intimate skin conditioner veil of claim 1, wherein the main portion has a front transversal width (W1) and a rear transversal width (W2), wherein a ratio W1/W2 is 1.1-6.6.

11. The intimate skin conditioner veil of claim 1, wherein a ratio L1/L2 is 0.5-1.

12. The intimate skin conditioner veil of claim 1 wherein the length (L1) of the main portion is 60-170 mm, and the total longitudinal length (L2) of the veil is 60-220 mm.

13. The intimate skin conditioner veil of claim 1, wherein the main portion has a front transversal width (W1) of 100-240 mm and a rear transversal width (W2) of 25-95 mm.

14. The intimate skin conditioner veil of claim 1, having a Gurley stiffness of 5-300 mgf.

15. The intimate skin conditioner veil of claim 1, wherein the space creating layer is a combined layer comprising a loft layer and a top sheet, the loft layer being positioned between the garment facing layer and the top sheet.

16. The intimate skin conditioner veil of claim 15, wherein the loft layer of the space creating layer has a basis weight of 15-100 gsm and a thickness of 0.5-3.5 mm.

17. The intimate skin conditioner veil of claim 1, wherein the space creating layer is a multilayer layer comprising a loft portion and a top sheet portion, the loft portion being positioned between the garment facing layer and the top sheet portion.

18. The intimate skin conditioner veil of claim 1, wherein the garment facing layer is breathable.

19. The intimate skin conditioner veil of claim 18, having a moisture vapour transmission rate of 1000-6000 $g/m^2/24\ h$.

20. The intimate skin conditioner veil of claim 1, further comprising a head portion extending between the front straight line and the front edge, wherein the head portion comprises at least one protuberance having a convex shape.

* * * * *